(12) United States Patent
Lafferrere et al.

(10) Patent No.: US 9,637,479 B2
(45) Date of Patent: May 2, 2017

(54) TARTRATE SALT OF 5-CHLORO-THIOPHENE-2-CARBOXYLIC ACID [(S)-2-[2-METHYL-3-(2-OXO-PYRROLIDIN-1-YL)-BENZENESULFONYLAMINO]-3-(4-METHYL-PIPERAZIN-1-YL)-3-OXO-PROPYL]AMIDE

(71) Applicant: SANOFI, Paris (FR)

(72) Inventors: Laurent Lafferrere, Paris (FR); Sébastien Villion, Paris (FR); Sandrine Gauthier, Paris (FR); André Bourbon, Paris (FR)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 14/786,953

(22) PCT Filed: Apr. 25, 2014

(86) PCT No.: PCT/EP2014/058513
§ 371 (c)(1),
(2) Date: Oct. 23, 2015

(87) PCT Pub. No.: WO2014/174102
PCT Pub. Date: Oct. 30, 2014

(65) Prior Publication Data
US 2016/0102082 A1    Apr. 14, 2016

(30) Foreign Application Priority Data
Apr. 26, 2013 (EP) .................................... 13305556

(51) Int. Cl.
*C07D 409/14* (2006.01)
*C07C 59/255* (2006.01)
*C07D 409/12* (2006.01)

(52) U.S. Cl.
CPC .......... *C07D 409/14* (2013.01); *C07C 59/255* (2013.01); *C07D 409/12* (2013.01)

(58) Field of Classification Search
CPC .... C07D 333/40; C07D 409/14; C07C 59/255
See application file for complete search history.

(56) References Cited

U.S. PATENT DOCUMENTS

2011/0112075 A1*  5/2011  Follmann .............. C07D 333/40
                                                       514/217.05

FOREIGN PATENT DOCUMENTS

WO    WO-2009/103440 A1    8/2009

OTHER PUBLICATIONS

Meneyrol et al., J. Med. Chem. 56, 9441-56 (2013).*
International Search Report mailed on Jun. 5, 2014, for PCT Application No. PCT/EP2014/058513, filed on Apr. 25, 2014, four pages.

* cited by examiner

*Primary Examiner* — Theodore R West
(74) *Attorney, Agent, or Firm* — Morrison & Foerster LLP

(57) ABSTRACT

The invention relates to the tartrate salt of 5-chloro-thiophene-2-carboxylic acid [(S)-2-[2-methyl-3-(2-oxo-pyrrolidin-1-yl)-benzenesulfonylamino]-3-(4-methyl-piperazin-1-yl)-3-oxo-propyl]amide, to its crystalline form, to its preparation and to its therapeutic use.

6 Claims, 1 Drawing Sheet

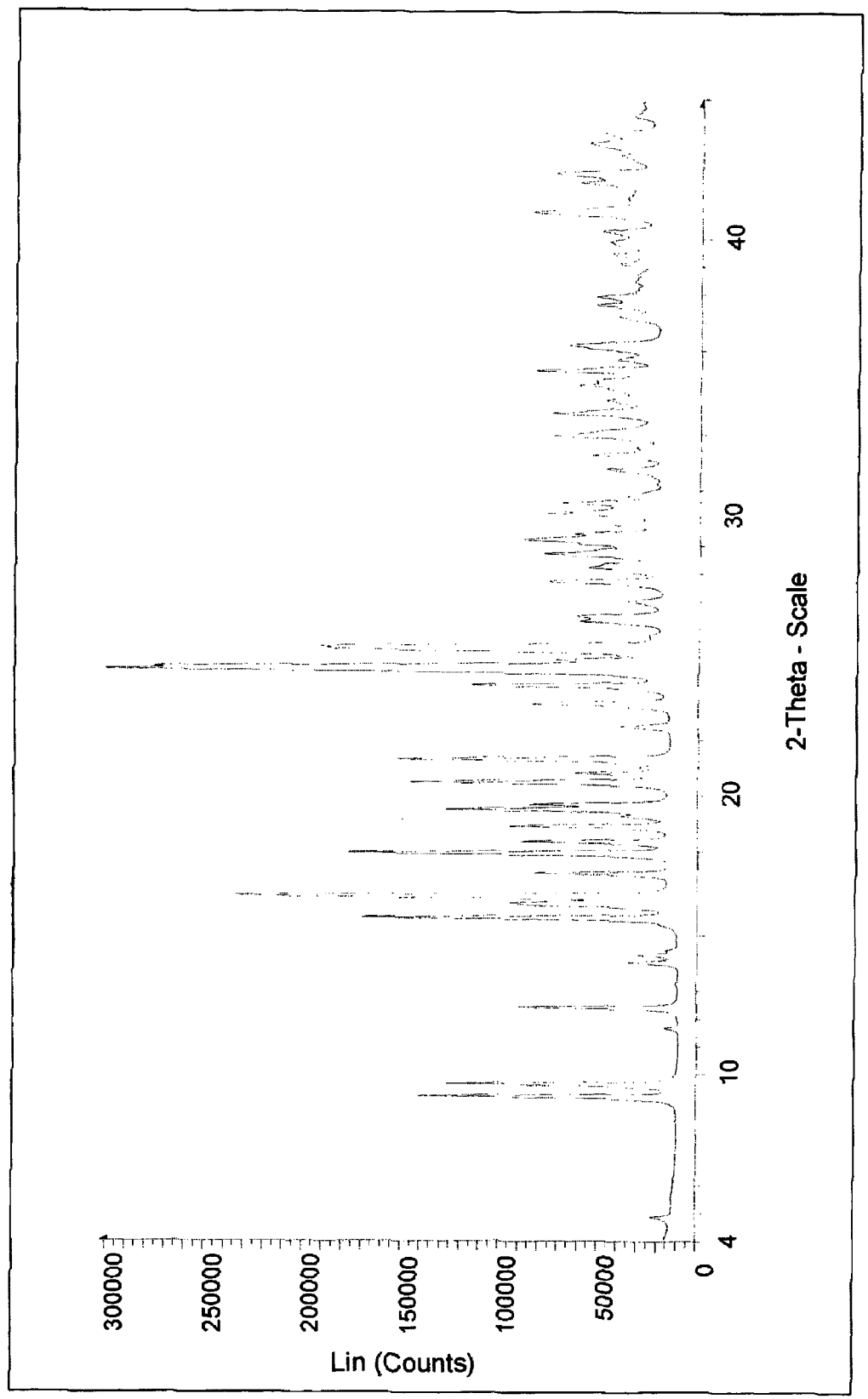

TARTRATE SALT OF 5-CHLORO-THIOPHENE-2-CARBOXYLIC ACID [(S)-2-[2-METHYL-3-(2-OXO-PYRROLIDIN-1-YL)-BENZENESULFONYLAMINO]-3-(4-METHYL-PIPERAZIN-1-YL)-3-OXO-PROPYL]AMIDE

CROSS REFERENCE TO RELATED APPLICATIONS

This application is a National Phase application under 35 U.S.C. §371 of International Application No. PCT/EP2014/058513 filed Apr. 25, 2014, which claims priority benefit to EP Application No. 13305556.6 filed Apr. 26, 2013, the disclosures of which are herein incorporated by reference in their entirety.

The invention relates to a novel salt of 5-chloro-thiophene-2-carboxylic acid [(S)-2-[2-methyl-3-(2-oxo-pyrrolidin-1-yl)-benzenesulfonylamino]-3-(4-methyl-piperazin-1-yl)-3-oxo-propyl]amide, to its crystalline form, to its preparation and to its therapeutic use.

5-chloro-thiophene-2-carboxylic acid [(S)-2-[2-methyl-3-(2-oxo-pyrrolidin-1-yl)-benzenesulfonylamino]-3-(4-methyl-piperazin-1-yl)-3-oxo-propyl]amide corresponds to the compound of formula (I) below:

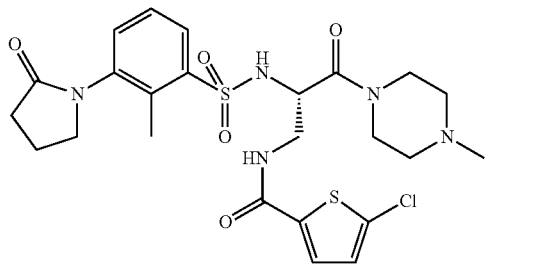

Formula (I)

The compound of formula (I) in its hydrochloride form, and a process for its preparation are described in the document WO 2009/103440.

This compound, among other chlorothiophene-amides, is described as an inhibitor of coagulation factors Xa and thrombin.

However, the free base of the compound of formula (I), as well as its hydrochloride salt as obtained according to WO 2009/103440 are both amorphous and therefore hardly industrially processable.

Thus, there is a need for an easily processable inhibitor of coagulation factors Xa and thrombin.

It has now been found that the salt of the L-2,3-dihydroxybutanedioic acid (also known as L-tartaric acid) of this same compound exhibits advantageous properties, which renders it particularly suitable for use thereof as active principle in a medicament.

A subject matter of the invention is thus the salt of the L-tartaric acid (or L-tartrate salt) of 5-chloro-thiophene-2-carboxylic acid [(S)-2-[2-methyl-3-(2-oxo-pyrrolidin-1-yl)-benzenesulfonylamino]-3-(4-methyl-piperazin-1-yl)-3-oxo-propyl]amide, its preparation and its therapeutic application.

Another subject matter of the invention is the crystalline form of the L-tartaric acid salt of 5-chloro-thiophene-2-carboxylic acid [(S)-2-[2-methyl-3-(2-oxo-pyrrolidin-1-yl)-benzenesulfonylamino]-3-(4-methyl-piperazin-1-yl)-3-oxo-propyl]amide, the physicochemical characteristics of which are described below.

Characterization of the Crystalline Form

X-Ray Diffractogram

The powder X-ray diffractogram was recorded starting from the powder samples of the L-tartrate salt of the compound of formula (I).

The analysis was carried out on the D8 Advance diffractometer (Bruker-Siemens) equipped with an Anton-Paar TKK temperature chamber exhibiting a set-up in reflection, possessing focusing geometry of Bragg-Brentano type (θ-θ)

A copper anticathode tube provides the incident radiation ($\lambda K\alpha 1$=1.5406 and 1.5444 angströms).

The recording of the diagrams at ambient temperature takes place at from 4 to 45 degrees in 2θ.

Characteristic lines of the diffractogram are given in the table below

TABLE 1

| Angle - 2 Theta ° | Relative Intensity % |
| --- | --- |
| 9.158 | 46.6 |
| 9.612 | 41.7 |
| 12.374 | 30.0 |
| 15.602 | 56.3 |
| 16.117 | 31.2 |
| 16.379 | 77.6 |
| 17.923 | 58.6 |
| 18.893 | 31.4 |
| 19.492 | 42.3 |
| 20.480 | 48.2 |
| 21.312 | 50.7 |
| 23.958 | 38.0 |
| 24.539 | 100.0 |
| 24.621 | 91.8 |
| 25.298 | 63.4 |
| 25.360 | 63.5 |

The diffractogram of the L-tartrate salt of the compound of formula (I) is presented in the FIG. 1.

The L-tartrate salt of the compound of formula (I) is a crystalline solid. The diffractogram indexing shows that it is pure crystalline phase (space group P21; cell volume 1618 Å$^3$).

Infrared Spectrum

The infrared (IR) spectrum of the L-tartrate of the compound of formula (I) was recorded on a Nexus IRTF spectrometer between 4000 and 400 cm$^{-1}$, with a resolution of 4 cm$^{-1}$. This spectrum is characterized by the absorption bands given in the table below.

TABLE 2

| λ (cm$^{-1}$) |
| --- |
| 3223 |
| 1684 |
| 1556 |
| 1334 |
| 1159 |
| 795 |

Thermogram

The differential thermodynamic analysis carried out on the compound of the invention did not exhibit any thermal event before melting at 203.9° C.

Another subject matter of the invention is a process for the preparation of the tartrate salt of 5-chloro-thiophene-2-carboxylic acid [(S)-2-[2-methyl-3-(2-oxo-pyrrolidin-1-yl)-benzenesulfonylamino]-3-(4-methyl-piperazin-1-yl)-3-oxo-propyl]amide and of its crystalline form.

In accordance with the invention the tartrate salt of the invention can be prepared in a salt formation reaction, by reacting the compound of formula (I) in its free form with tartaric acid in a solvent.

The compound of formula (I) can be obtained according to the following process:

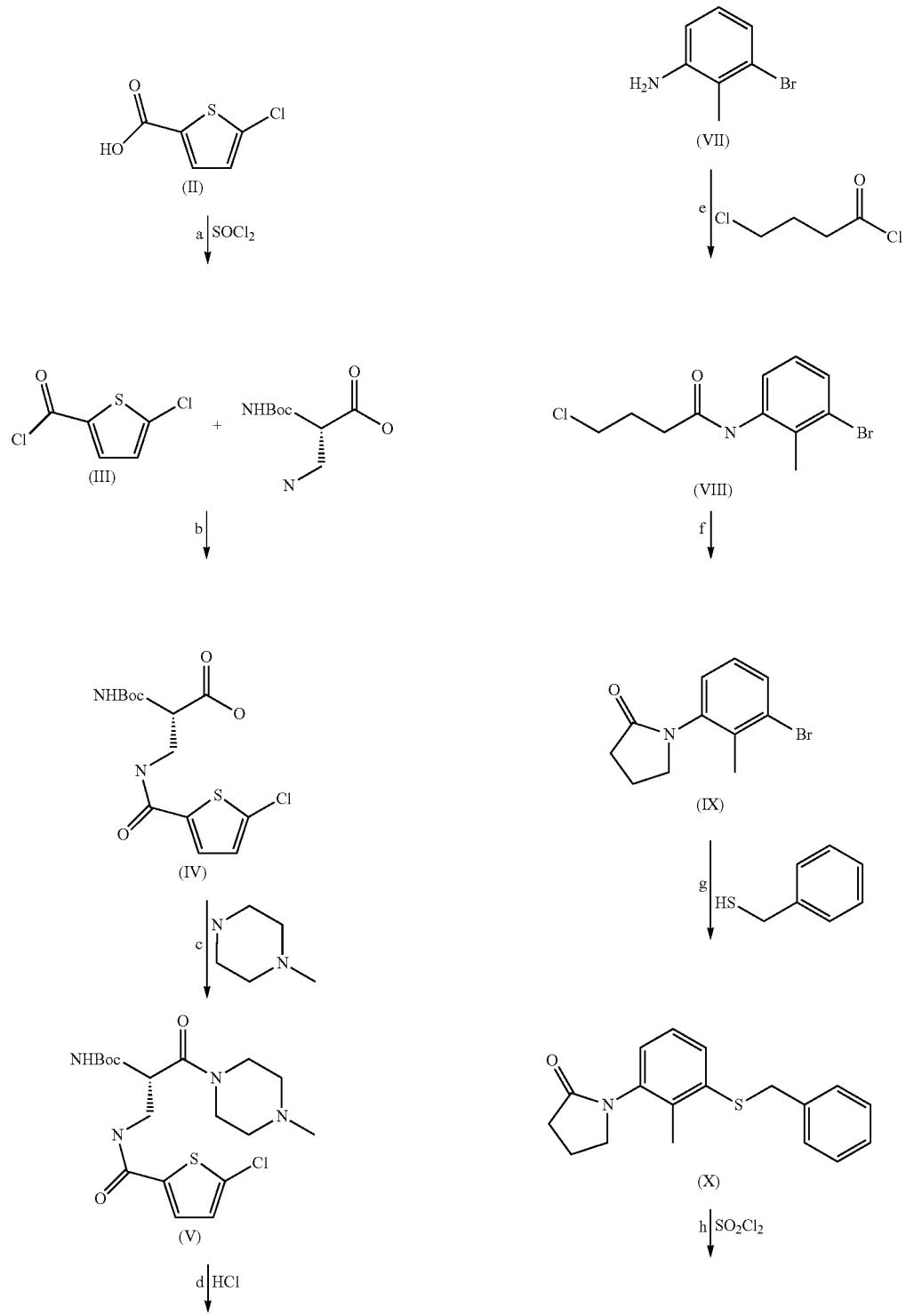

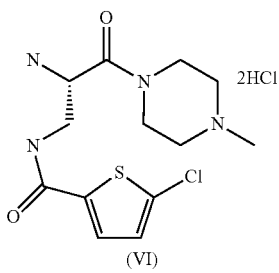

(VI)

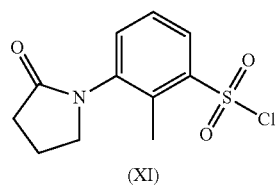

(XI)

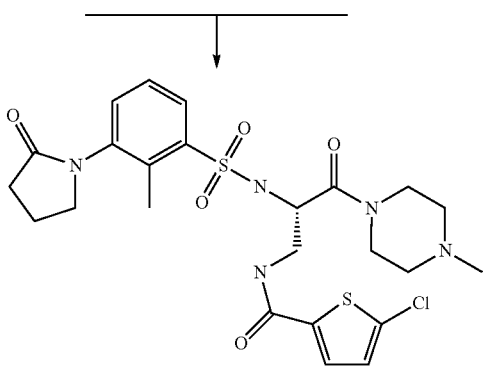

Alternatively, the compound of formula (I) can be prepared according to one of the processes described in WO 2009/103440.

The example which follows describes the preparation of the tartrate salt of the compound of formula (I) of the invention according to the general scheme described above.

The following abbreviations and empirical formulae are used:
EtOAc ethyl acetate
Boc tert-butoxycarbonyl
DAP diaminopimelic acid
T3P propylphosphonic anhydride
EtOH ethanol
DIEA N,N-diisopropylethylamine
HCl hydrogen chloride
MeTHF 2-methyltetrahydrofuran
t-BuOK potassium tert-butoxide
THF tetrahydrofuran
iPrOH isopropanol
° C. degrees Celsius Step (a): 5-Chloro-thiophene-2-carbonyl chloride (Compound III)

From 100 g (1.1 eq) of 5-Chloro-thiophene-2-carboxylic acid of formula (II), the acid chloride of formula (III) was obtained by reaction with 1.5 eq of thionyl chloride in 1.4 vol of toluene at 80° C.

Step (b): 2-tert-Butoxycarbonylamino-3-[(5-chloro-thiophene-2-carbonyl)-amino]-propionic acid (Compound IV)

The reaction medium comprising the acid chloride (compound III) obtained in step (a) was flown on a solution at 5° C. comprising 1 eq of Boc-DAP-OH in the presence of 3.3 eq of NaOH 30% in 3 vol of THF and 1.2 vol of water in order to obtain the compound of formula (IV), which was isolated after evaporation.

Step (c): [1-{[(5-Chloro-thiophene-2-carbonyl)-amino]-methyl}-2-(4-methyl-piperazin-1-yl)-2-oxo-ethyl]carbamic acid tert-butyl ester (Compound V)

Compound (V) was obtained by coupling 3 eq of compound (IV) obtained in step (b) with methylpiperazine with 1.5 eq of T3P as a coupling agent in solution in EtOAc during 18 hours.

Compound (V) was then extracted with EtOAc then isolated by crystallization in 1.5 to 2 vol of EtOAc.

Step (d): 5-Chloro-thiophene-2-carboxylic acid [2-amino-3-(4-methyl-piperazin-1-yl)-3-oxo-propyl]-amide (Compound VI)

Compound (VI) was obtained by hydrolyzing the Boc function of compound (V).

Compound (V) in 6.5 vol of EtOH and 0.36 of water was flown on 3 eq of heated (70° C.) aqueous HCl 12N during 1 hour.

Step (e): N-(3-Bromo-2-methyl-phenyl)-4-chloro-butyramide (Compound VIII)

Compound (VIII) was prepared by acylating 200 g of 3-bromo-methylaniline (compound VII) with 1 eq of 4-chlorobutyryl chloride in the presence of 1.2 eq DIEA in 5 vol of THF, at 20° C.

After 2 hours the resulting mixture was flown onto 13 eq of water at 15° C., leading to the precipitation of compound VIII.

Step (f): 1-(3-Bromo-2-methyl-phenyl)-pyrrolidin-2-one (Compound IX)

Compound (IX) was obtained by cyclisation of 290 g of compound (VIII) in presence of 1.2 eq of tBuOK in 10 vol of MeTHF, at 10° C.

Step (g): 1-(3-Benzylsulfanyl-2-methyl-phenyl)-pyrrolidin-2-one (Compound X)

Compound (X) was obtained from 20 g of compound (IX) in presence of 1.2 eq of benzylmercaptan, 0.06 eq of phosphine, 0.03 of Pd(0) and 2 eq of DIEA in 8 vol of toluene for 4 hours at 100° C.

Step (h): 2-Methyl-3-(2-oxo-pyrrolidin-1-yl)-benzenesulfonyl chloride (Compound XI)

Compound (XI) was obtained by oxidation of compound (IX), in presence of 4 eq of sulfuryl chloride in 5.7 eq of acetic acid and 0.3 vol of water.

Step (i): 5-chloro-thiophene-2-carboxylic acid [(S)-2-[2-methyl-3-(2-oxo-pyrrolidin-1-yl)-benzenesulfonylamino]-3-(4-methyl-piperazin-1-yl)-3-oxo-propyl]amide (Compound of formula (I))

The compound of formula (I) was obtained by coupling compound (VI) and compound (XI).

A solution of compound (XI) was flown onto 208.85 g of compound (VI) in presence of 8 eq of $K_2CO_3$ in 3 vol of water and 2 vol of dichloromethane at 10° C., thus obtaining the compound of formula (I) in its free form.

The obtained compound of formula (I) was an amorphous product.

Salt Formation

Once the compound of formula (I) in its free form was obtained, it was subjected to a crystallization reaction in order to obtain its L-tartrate salt.

The compound of formula (I) obtained in step (i) was subjected to a crystallization reaction.

In a flask, 0.5 g of the compound of formula (I) in 4 ml of water then 0.132 g of L(+)tartaric acid were heated for total solution, then kept under stirring for 24 hours.

The formed solid was then filtrated and dried, obtaining then a white powder of the compound of the invention.

L-tartrate salt of the compound of formula (I) thus obtained has a very high rate of purity (98.9%).

Tests

As mentioned before, it is to be noted that the compound of formula (I) in its hydrochloride salt form is amorphous and that no attempts to crystallize it were successful.

Unexpectedly, it has specifically been demonstrated that the tartrate salt of the compound of formula (I) has properties of purity, of stability and of solubility which are improved with respect to the same compound in the L-lactate and L-sodium forms (both crystalline salts).

Physical Properties

The physical properties of the compound of formula (I) in its sodium, L-lactate and L-tartrate salts are summarized in the table below.

TABLE 3

|  | Sodium salt | L-lactate salt | L-tartrate salt |
| --- | --- | --- | --- |
| Physical state (ambient conditions) | Monohydrate | Non stoichiometric hydrate | Anhydrous |
| Hygroscopicity | Highly hygroscopic | Hygroscopic | Slightly hygroscopic |
| Water uptake 80% RH 25° C. | 31.5% | 2.5% | 0.9% |
| Behavior under saturated humidity 80° C. | Deliquescence after 24 hours | Gel formation-amorphous after 24 hours | Stable 7 days |

These results show that the L-tartrate salt exhibits better hygroscopicity, water uptake and stability under stress conditions than the sodium and L-lactate salts, which means that the L-tartrate salt can be easier handled and stored.

Crystallization Characteristics:

Several characteristics of the crystallization of the compound of formula (I) in its sodium, L-lactate and L-tartrate salts were analyzed in two different solvents: a non polar solvent (ethyl acetate or EtOAc) and a polar protic solvent (isopropanol or iPrOH).

The results are described in the table below.

TABLE 4

|  | Sodium salt | L-lactate salt | L-tartrate salt |
| --- | --- | --- | --- |
| Kinetic of crystallisation | 1 to 3 days | 1 hour in AcOEt 1 day in iPrOH | 2 hours |
| Gumming | Not observed | Observed in AcOEt Not observed in iPrOH | Not observed |
| Filtration | Quick | Tedious | Quick |
| Yield | 5% in AcOEt 53% in iPrOH | 71% in AcOEt 53% in iPrOH | 75% |

In the light of the results above, it is found that the L-tartrate salt of the compound of formula (I) has better crystallization characteristics than the L-lactate and the sodium salt in both tested solvents.

In particular, the crystallization of the L-tartrate salt is quick, with a good yield and the obtained product is easily filtrated.

Thus, these results demonstrate the good crystallization processability of the L-tartrate salt of the compound of formula (I).

Test of Stability in the Solid State.

The sodium, L-lactate and L-tartrate salts of the compound of formula (I) were analyzed after one week of storage, at:

80° C.

80° C. and under saturated humidity,

The results are described in the table below.

TABLE 5

| Stress degradation conditions | 80° C./dry | 80°/saturated humidity |
| --- | --- | --- |

TABLE 5-continued

| Sodium salt | stable* | huge degradation |
| --- | --- | --- |
| L-lactate salt | stable* | slight degradation |
| L-tartrate salt | stable* | stable |

*stable optically, chemically and physically

In the light of the results obtained above, it is found that the sodium and the L-lactate salt of the compound of formula (I) are not stable under the effect of heat and humidity, so that they have to be stored protected from humidity.

In contrast, the L-tartrate salt remains unchanged. These results thus demonstrate a greater stability of the L-tartrate salt of the compound of formula (I) under the tested conditions.

Test of Solubility

The solubility of sodium, L-lactate and L-tartrate salts of the compound of formula (I) was analyzed in different buffers.

The results are described in table below (solubility of the tested compound is expressed in mg/ml).

TABLE 6

| | Tested compound | | |
| --- | --- | --- | --- |
| Solubilsation media | Sodium salt | L-lactate salt | L-tartrate salt |
| 0.1N HCl | >10 | >10 | >10 |
| 0.1M pH = 4 phosphate buffer | 8.9 | >10 | >10 |
| 0.1M pH = 6.5 phosphate buffer | 6.5 | >10 | >10 |
| 0.1M pH = 7.4 phosphate buffer | 6.9 | 9.8 | >10 |
| 0.2M pH = 9 hydregenocarbonate buffer | >10 | 8.5 | 8.3 |
| Purified water | >10 | >10 | >10 |

In the light of the results obtained above, it is found that all the three tested salts are highly soluble in the all studied media, and the L-tartrate salt is the most soluble of them.

Test of Stability in Solution

The sodium, L-lactate and L-tartrate salts of the compound of formula (I) were analyzed after one week of storage in a strong oxidizing solution: the three compounds were maintained in a solution of $H_2O_2$ at 0.3%, at room temperature.

After either 6 hours or one week, the proportion of the main N-oxide impurity of the compound of formula (I)

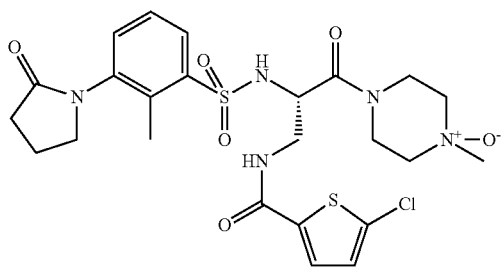 [SMILES: Cc1c(N2CCCC2=O)cccc1S(=O)(=O)N[C@@H](CNC(=O)c1ccc(Cl)s1)C(=O)N1CC[N+](C)([O-])CC1]

was measured.

The results are described in the table below.

TABLE 7

| | Sodium salt | L-lactate salt | L-tartrate salt |
| --- | --- | --- | --- |
| % of impurity | 25.4% after 6 hours | 6.9% after 1 week | 0.77% after 1 week |

In view of the results obtained above, it is found that the L-tartrate salt is more stable in an oxidative solution than the L-lactate and the sodium salts of the compound of formula (I).

The physicochemical properties of the L-tartrate salt of the compound of formula (I) allow it to be stored under normal conditions, without excessively restrictive precautions with respect to the presence of light, the temperature and the humidity and therefore to be easily processed.

The tartrate salt of 5-chloro-thiophene-2-carboxylic acid [(S)-2-[2-methyl-3-(2-oxo-pyrrolidin-1-yl)-benzenesulfonylamino]-3-(4-methyl-piperazin-1-yl)-3-oxo-propyl]amide is an inhibitor of coagulation factors Xa and thrombin.

As such, it can be used in the preparation of medicaments, in particular of medicaments which are inhibitors of coagulation factors Xa and thrombin.

Accordingly, in another of its aspects, the invention provides medicaments which comprise the L-tartrate salt of 5-chloro-thiophene-2-carboxylic acid [(S)-2-[2-methyl-3-(2-oxo-pyrrolidin-1-yl)-benzenesulfonylamino]-3-(4-methyl-piperazin-1-yl)-3-oxo-propyl]amide.

These medicaments are employed therapeutically, especially in the treatment and prevention of cardiovascular disorders, thromboembolic diseases or restenoses.

These medicaments are also employed therapeutically for the inhibition of factor Xa and thrombin or for influencing blood coagulation or fibrinolysis or for the therapy or prophylaxis of the diseases mentioned above or below, for example for use in the therapy and prophylaxis of cardiovascular disorders, thromboembolic diseases or restenoses, and to methods of treatment aiming at such purposes including methods for said therapies and prophylaxis.

These medicaments are also employed in the treatment of disease states such as abnormal thrombus formation, acute myocardial infarction, unstable angina, thromboembolism, acute vessel closure associated with thrombolytic therapy or percutaneous transluminal coronary angioplasty (PTCA), transient ischemic attacks, stroke, intermittent claudication or bypass grafting of the coronary or peripheral arteries, vessel luminal narrowing, restenosis post coronary or venous angioplasty, maintenance of vascular access patency in long-term hemodialysis patients, pathologic thrombus formation occurring in the veins of the lower extremities following abdominal, knee or hip surgery, pathologic thrombus formation occurring in the veins of the lower extremities following abdominal, knee and hip surgery, a risk of pulmonary thromboembolism, or disseminated systemic intravascular coagulatopathy occurring in vascular systems during septic shock, certain viral infections or cancer.

The compounds of the present invention can also be used to reduce an inflammatory response. Examples of specific disorders for the treatment or prophylaxis of which the compounds of the invention can be used are coronary heart disease, myocardial infarction, angina pectoris, vascular restenosis, for example restenosis following angioplasty like PTCA, adult respiratory distress syndrome, multi-organ failure and disseminated intravascular clotting disorder.

Examples of related complications associated with surgery are thromboses like deep vein and proximal vein thrombosis, which can occur following surgery.

According to another of its aspects, the present invention relates to pharmaceutical compositions comprising, as active principle, the L-tartrate salt of 5-chloro-thiophene-2-carboxylic acid [(S)-2-[2-methyl-3-(2-oxo-pyrrolidin-1-yl)-benzenesulfonylamino]-3-(4-methyl-piperazin-1-yl)-3-oxo-propyl]amide according to the invention. These pharmaceutical compositions contain an effective dose of the compound according to the invention and also at least one pharmaceutically acceptable excipient.

The said excipients are chosen, according to the pharmaceutical form and the desired mode of administration, from the usual excipients known to those skilled in the art.

The invention claimed is:

1. An L-tartrate salt of 5-chloro-thiophene-2-carboxylic acid [(S)-2-[2-methyl-3-(2-oxo-pyrrolidin-1-yl)-benzenesulfonylamino]-3-(4-methyl-piperazin-1-yl)-3-oxo-propyl]amide, which is crystalline.

2. The L-tartrate salt of 5-chloro-thiophene-2-carboxylic acid [(S)-2-[2-methyl-3-(2-oxo-pyrrolidin-1-yl)-benzenesulfonylamino]-3-(4-methyl-piperazin-1-yl)-3-oxo-propyl]amide according to claim 1, which has a powder X-ray diffraction pattern comprising peaks at angles 2 theta of about 9.2°, 9.6°, 12.4°, 15.6°, 16.1°, 16.4°, 17.9°, 18.9°, 19.5°, 20.5°, 21.3°, 24.0°, 24.5°, 24.6°, 25.3°, and 25.4°.

3. A process for the preparation of an L-tartrate salt of 5-chloro-thiophene-2-carboxylic acid [(S)-2-[2-methyl-3-(2-oxo-pyrrolidin-1-yl)-benzenesulfonylamino]-3-(4-methyl-piperazin-1-yl)-3-oxo-propyl]amide, which is crystalline, comprising reacting a free base form of 5-chloro-thiophene-2-carboxylic acid [(S)-2-[2-methyl-3-(2-oxo-pyrrolidin-1-yl)-benzenesulfonylamino]-3-(4-methyl-piperazin-1-yl)-3-oxo-propyl]amide with L-tartaric acid in a solvent.

4. The process according to claim 3, further comprising reacting 5-chloro-thiophene-2-carboxylic acid [2-amino-3-(4-methyl-piperazin-1-yl)-3-oxo-propyl]-amide with 2-methyl-3-(2-oxo-pyrrolidin-1-yl)-benzenesulfonyl chloride to produce the free base form of 5-chloro-thiophene-2-carboxylic acid [(S)-2-[2-methyl-3-(2-oxo-pyrrolidin-1-yl)-benzenesulfonylamino]-3-(4-methyl-piperazin-1-yl)-3-oxo-propyl]amide.

5. A pharmaceutical composition comprising an L-tartrate salt of 5-chloro-thiophene-2-carboxylic acid [(S)-2-[2-methyl-3-(2-oxo-pyrrolidin-1-yl)-benzenesulfonylamino]-3-(4-methyl-piperazin-1-yl)-3-oxo-propyl]amide, which is crystalline, and at least one pharmaceutically acceptable excipient.

6. A method of treating or preventing a cardiovascular disorder, a thromboembolic disease or a restenosis in a patient in need thereof, comprising administering to the patient a therapeutically effective amount of the L-tartrate salt of 5-chloro-thiophene-2-carboxylic acid [(S)-2-[2-methyl-3-(2-oxo-pyrrolidin-1-yl)-benzenesulfonylamino]-3-(4-methyl-piperazin-1-yl)-3-oxo-propyl]amide according to claim 1.

* * * * *